United States Patent [19]

Eriksen et al.

[11] Patent Number: 5,286,404
[45] Date of Patent: Feb. 15, 1994

[54] LIQUID ENZYMATIC DETERGENT COMPOSITION

[75] Inventors: Nina Eriksen; Gitte Pedersen, both of Frederiksberg, Denmark

[73] Assignee: Novo Nordisk A/S, Bagsvaerd, Denmark

[21] Appl. No.: 835,907

[22] PCT Filed: Oct. 12, 1990

[86] PCT No.: PCT/DK90/00263
§ 371 Date: Feb. 27, 1992
§ 102(e) Date: Feb. 27, 1992

[87] PCT Pub. No.: WO91/05840
PCT Pub. Date: May 2, 1991

[30] Foreign Application Priority Data

Oct. 13, 1989 [DK] Denmark .............................. 5111/89
Jan. 31, 1990 [DK] Denmark .............................. 0257/90

[51] Int. Cl.$^5$ ........................ C11D 17/00; C12N 9/96

[52] U.S. Cl. ...................... 252/174.12; 252/DIG. 12; 435/188

[58] Field of Search ................ 252/174.12, DIG. 12; 435/188

[56] References Cited

FOREIGN PATENT DOCUMENTS 63-139997  6/1988  Japan.
1280497   7/1972  United Kingdom.

Primary Examiner—Anthony McFarlane
Assistant Examiner—Nhat D. Phan
Attorney, Agent, or Firm—Steve T. Zelson; Elias J. Lambiris

[57] ABSTRACT

The solubility of an enzyme in a liquid detergent can be improved by chemical modification of free primary amino groups in the enzyme while still preserving the enzyme activity. The modification preferably involves aldehyde treatment, acylation, or alkylation of the amino groups.

33 Claims, No Drawings

LIQUID ENZYMATIC DETERGENT COMPOSITION

TECHNICAL FIELD

This invention relates to a liquid enzymatic detergent composition and to an enzymatic detergent additive in the form of a stabilized liquid for use therein. The invention also relates to a method of increasing the solubility of an enzyme, particularly in the preparation of a liquid enzymatic detergent or a liquid enzymatic detergent additive.

BACKGROUND ART

Enzymes are commonly incorporated in liquid detergents to improve detergency. The most commonly used detergent enzymes are proteases, mainly alkaline Bacillus proteases such as subtilisin Carlsberg. The prior art deals extensively with the formulation of liquid enzymatic detergents, particularly with improving the stability of the enzyme during storage. One recent example is EP 352,244.

In general, the enzyme should be fully dissolved in the liquid detergent to prevent phase separation during storage and to ensure that the enzyme activity is immediately available during washing.

We have found that in some liquid detergents, the enzyme is not fully soluble and may precipitate. It is the object of the invention to provide a liquid enzymatic detergent composition with improved enzyme solubility, an enzymatic detergent additive for use therein, and a method of improving the solubility of an enzyme without serious loss of enzyme activity.

DISCLOSURE OF INVENTION

We have, surprisingly, found that by chemical modification of free primary amino groups in an enzyme, the solubility of the enzyme can be improved while the enzyme activity is preserved. The modification preferably involves aldehyde treatment, acylation or alkylation.

It is known that aldehydes can react with primary amino groups in enzymes, and treatment of enzyme with glutaraldehyde has been widely used for immobilization of enzymes, i.e. for preparing a water insoluble enzyme product (e.g. U.S Pat. No. 3,980,521, JP-B 50-037274). It is also known from DE-A 2,919,622 that a water-insoluble product can be obtained by treatment of a protease with a polysaccharide derivative containing aldehyde groups such as dialdehyde starch. Further, it is known from J. Boudrant et al., Biotech. and Bioeng., XVIII, 1719-34 (1976) that aldehyde treatment of a typical detergent enzyme converts part of the enzyme protein into an insoluble fraction. GB 1,280,497 discloses treatment of enzyme with e.g. glutaraldehyde and removal of insoluble residue to improve the stability of the enzyme when added to a solution of powder detergent. There is, however, no suggestion in the prior art that such treatment of an enzyme can be used to increase its solubility.

Accordingly, the invention provides a liquid enzymatic detergent composition and an enzymatic detergent additive in the form of a stabilized liquid, each characterized by comprising dissolved therein an enzyme containing chemically modified primary amino groups.

Further, the invention provides a method of increasing the solubility of an enzyme containing free primary amino groups, said method comprising chemical modification of part or all of said primary amino groups.

DETAILED DESCRIPTION OF INVENTION

Enzyme

Besides the terminal amino group, most enzymes, in particular most detergent enzymes, contain lysine with free primary amino ($-NH_2$) groups. The invention may be used for modifying any enzyme, provided it contains free primary amino groups, preferably at least 2, and most preferably at least 4 free primary amino groups per molecule. The enzyme typically has molecular weight 20,000–100,000, especially 20,000–60,000, and isoelectric point 7–12. The enzyme may be a protease, an amylase, a lipase, a peroxidase or a cellulase, especially a subtilisin (an alkaline Bacillus protease), e.g. Subtilisin Carlsberg, derived from *B. licheniformis* (e.g. Alcalase®, product of Novo Nordisk A/S), Savinase® (product of Novo Nordisk, produced from alkalophilic Bacillus according to U.S. Pat. No. 3,723,250) or a mutant subtilisin such as those described in WO 89/06279 or DK 0541/90. Subtilisin Carlsberg has molecular weight 27,000, pI around 8.3 and the molecule contains 10 primary amino groups (the N-terminal and 9 lysine groups). The detergent of the invention typically contains 2–40 μmole of modified enzyme per kg.

Chemical modification

According to the invention, the enzyme may be modified by any method acting on primary amino groups, particularly by reaction with an aldehyde, by acylation or by alkylation.

The enzyme is preferably treated in aqueous solution at a concentration of 0.1–5 mM. The enzyme to be treated is preferably largely free from other proteins and other compounds with primary amino groups as these may interfere by reacting with the modifying reactant. In general, the amount of the modifying reactant may correspond to 0.1–3 reactive groups per primary amino group, preferably 0.2–2 and most preferably 0.4–1.4.

When using a monofunctional reactant, it may be preferable to use an excess of reactant, e.g. 1–5 times of the stoichiometric.

When using a bifunctional (or polyfunctional) reactant it may be preferable, in order to improve the solubility, to minimize formation of oligomers by intermolecular reactions. The formation of oligomers may be minimized by using a relatively low concentration of enzyme, e.g. 0.1–1 mM, and/or by using essentially the stoichiometric amount or less of the bi/polyfunctional reactant, e.g. 10–100% of the stoichiometric. If oligomers precipitate after the treatment, this precipitate may be removed (e.g. by centrifugation) to obtain modified enzyme consisting mostly of monomer.

Aldehyde treatment may be made using an aliphatic or aromatic mono- or dialdehyde, e.g. formaldehyde, glutaraldehyde or o-phthalic aldehyde. The treatment is preferably carried out at pH in the range 5–10 and a temperature of 0°–70° C., conveniently near ambient temperature. The mixture of enzyme and aldehyde should be left until the reaction is essentially complete (as indicated by stable pH), typically 0.5–8 hours.

Acylation may be made by use of an anhydride of a mono- or dicarboxylic acid, e.g. acetic, propionic, butyric, valeric, caprylic, maleic or succinic anhydride.

Alkylation of primary amino groups may be achieved e.g. by reductive treatment with an aldehyde, such as those mentioned above. An example is reductive methylation.

Detergent additive

The enzymatic detergent additive of the invention contains an enzyme stabilizer to improve the storage stability. Many such enzyme stabilizers are known in the art, e.g. a polyol such as propylene glycol, typically used in an amount of 20-70%, e.g. according to U.S. Pat. Nos. 4,543,333 or 4,497,897.

Detergent

The invention is particularly applicable to the formulation of liquid detergent where it is desired to incorporate enzyme at a concentration that exceeds the solubility of the unmodified enzyme.

The invention particularly relates to a homogeneous concentrated liquid detergent with water content of 20-50% (hereinafter, all percentages are by weight), especially 40-50%. The pH of the detergent may be 6-10.5, especially 7-9.

The detergent may contain 4-25% of $C_{10}$-$C_{16}$ alkyl or alkenyl succinate, especially 5-15% of said succinate. The detergent may further contain other builders, e.g. 0.5-6% citrate. The cation may be sodium, potassium, ammonium or mono-, di- or triethanol-ammonium.

The detergent may additionally contain 5-30%, especially 10-20% of anionic surfactant, such as alkyl benzene sulphonate, alpha-olefin sulphonate, dialkyl sulfosuccinate, alkyl sulphate, alkyl ethoxy sulphate, fatty acid soap or a combination of two or more of these. In each of these, the alkyl group may be linear $C_{10}$-$C_{18}$, and the cation may be sodium, potassium, ammonium or mono, di- or triethanol-ammonium.

The detergent may also contain 3-35%, especially 5-15% of nonionic surfactant, such as polyethoxylated alcohol or alkyl phenol.

The detergent may contain 2-20%, especially 2-10% of solvent, such as $C_1$-$C_4$ alcohol or polyol, e.g. ethanol or glycerol or a combination of two or more solvents.

The detergent may additionally contain 0.5-5% of one or more electrolytes, such as borate, carbonate, formate or chloride of sodium or potassium.

Specific examples of detergents according to the invention are obtained from the compositions given in EP 200,263, EP 212,723 and EP 223,306 (said three publications incorporated herein by reference) by including 12-16 μmole/kg, e.g. 15 μmole/kg of modified enzyme according to the invention, and optionally substituting dodecyl-succinate for dodecenyl-succinate.

EXAMPLES

Example 1

Phthaldialdehyde was added to a solution of enzyme (Alcalase) to prepare an aqueous system containing 63 mg/g (2.3 μmole/g) of enzyme and 1 mg/g (7.5 μmole/g) of aldehyde, i.e. a ratio of 0.65 aldehyde groups per primary amino group. The system also contained 25% of propylene glycol, 0.2% of calcium ions and 1.8% of formate ions. The pH was adjusted to 10 and the phthaldialdehyde reacted with the enzyme solution for approx. 5 hours. Afterwards the solution was filtered, pH adjusted to 5.5.

By measuring the protease activity before treatment with phthaldialdehyde and after treatment and pH adjustment, it was found that there had been no detectable loss of activity.

0.6% of this solution was added to a commercial liquid detergent ("Ariel" (batch 279A42), marketed by Procter & Gamble in Denmark). After storage for 6 weeks at both 25° C. and 35° C. no enzyme deposit was observed in the detergent. As a reference the same Alcalase which has not been treated with the aldehyde was added to the detergent (the same amount of active enzyme as for the aldehyde treated enzyme was added). After four days at 35° C. and one week at 25° C. needle-shaped enzyme deposit was observed.

Example 2

As Example 1 except that phthaldialdehyde was exchanged with 10 μmole/g of glutaraldehyde, i.e. a molar ratio of 0.87. After adding to the detergent the system was observed for 4 weeks and no enzyme deposit was found neither at 25° C. nor at 35° C.

Example 3

Glutaraldehyde was added to a solution of enzyme (Alcalase) to prepare an aqueous solution containing 87 mg/g (3.2 μmole/g) of enzyme and 1.16 mg/g (11.6 μmole/g) of aldehyde, i.e. a ratio of 0.73 aldehyde groups per primary amino group. The pH was kept at 7.5 throughout the treatment. The treatment was terminated when base consumption ceased, and the solution was filtered.

A formulation containing 25% propylene glycol, 0.2% Ca, 1.8% formate and pH 5.5 was prepared. 0.6% of this formulation was added to the same detergent as in Example 1, and after storage at 35° C. and 25° C. for 3 weeks no crystalline enzyme deposit was observed.

The molecular weight of the glutaraldehyde-treated Alcalase was determined by SDS-PAGE together with untreated Alcalase. The molecular weights of the two enzymes were found to be exactly the same, approx. 27,000.

Example 4

Glutaraldehyde was added to a solution of enzyme (Alcalase) to prepare an aqueous solution containing 60 mg/g (2.2 μmole/g) of enzyme and 0.90 mg/g (9.0 μmole/g) of aldehyde, i.e. a ratio of 0.82 aldehyde groups per primary amino group. The pH was kept at 7.5 throughout the treatment. The treatment was terminated when base consumption ceased.

A detergent with the following composition was used:

| | |
|---|---|
| Linear Alkyl Sulphonate (NANSA 1169/P) | 9.65% |
| Alcohol Ethoxylate (Dobanol 25-7) | 10.00% |
| 2-dodecenyl succinic anhydride | 13.60% |
| Citric acid | 0.85% |
| Oleic acid | 3.65% |
| Diethylenetriamine pentamethylene phosphonic acid | 0.80% |
| Coconut alkyl sulphate TEA salt | 3.30% |
| Ethanol, 96% | 3.00% |
| 1,2-propanediol | 1.70% |
| Monoethanolamine | 0.50% |
| Sodium formate | 0.95% |
| Calcium chloride ($CaCl_2$, $2H_2O$) | 0.06% |
| NaOH | 4.15% |
| Water | balance to 100% |
| pH | 7.6 |

The mixing procedures for the detergent, which take place at 80°-85° C., are as follows:

I: The following components are mixed in the mentioned order:

LAS, 1,2-propanediol, ethanol, coconut alkyl sulphate TEA salt and monoethanolamine. Afterward the NaOH and 2-dodecenyl succinic anhydride are added simultaneously. One half of the water, alcohol ethoxylate.

II: The other half of the water, sodium formate, calcium chloride, phosphonate and citric acid are mixed.

III: I+II+oleic acid are mixed.

0.6% of the aldehyde treated enzyme was added to the detergent. As reference, 0.6% of untreated enzyme was added to the same detergent.

After three days at 35° C. needle-shaped precipitate was observed in the reference detergent. No precipitate was observed in the detergent with the aldehyde-treated Alcalase.

Storage stability was determined by measuring residual enzyme activity at various times during storage at controlled temperature. No difference was seen between the detergent with modified enzyme and reference detergent.

Comparative washing tests showed the detergent with modified enzyme and the reference detergent to be equally effective for removal of proteinaceous soiling.

Example 5

1 g protease (Alcalase) was dissolved in 25 ml 0.1M borate buffer pH 7 at 0° C. 700 µl of a 100 mg/ml succinic anhydride solution in acetone was added portion wise (theoretically 2.1 equivalent anhydride/—$NH_2$ lysine group). pH was adjusted to 7 with 2M NaOH after each addition of succinic anhydride. The reaction was followed on an MonoS ion exchange. The reaction mixture was dialysed against water when no more free enzyme could be detected. The mixture was then freeze dried.

A stabilized liquid formulation was prepared, containing 55.55 mg modified enzyme per g, 25% propylene glycol, 0.2% calcium, 1.8% formic acid at pH 5.5. 0.6% of this formulation was added to the detergents described in Examples 1 and 4.

A reference was made by treating the enzyme in the same way, but without addition of succinic anhydride. 0.8% of the reference formulation was added to the detergents.

In the reference detergents, needle-shaped deposit was observed after 10 days storage at 35° C. and one month at 25° C. No deposit was observed in the detergents with modified enzyme according to the invention.

Example 6

10 g of an enzyme stock solution containing 55.5 mg pure enzyme (Alcalase), 25% propylene glycol, 0.2% calcium and 1.8% formic acid was adjusted from pH 5.2 to pH 8.0. 2 g of a 200 mM $NaBH_3CN$ solution was added. 73.97 mg of a 37% HCHO solution was then added portion wise (corresponding to 5 mole equivalents HCHO per mole lysine amino group). The reaction was conducted at room temperature for 2 hours. The pH was the adjusted to 5.2 with formic acid. No enzymatic activity was lost during the procedure. 80 mg of this formulation was added to 10 g of the detergents described in Examples 1 and 4. As reference, 80 mg of the enzyme stock solution added to 10 g of the same detergents.

After 1 week, needle-shaped enzyme deposit was observed in the reference detergents, whereas no deposit could be observed in the detergents with modified enzyme according to the invention.

Example 7

10 g of an enzyme stock solution containing 55.5 mg of pure enzyme (Alcalase), 25% propylene glycol, 0.2% Ca, 1.8% formic acid, was adjusted from 5.2 to 8.0. 1 g of a 200 mM $NaBH_3CN$ solution was added. 33.33 mg of a 50% Glutaraldehyde solution was then added portion wise (Corresponding to 0.91 mole glutaraldehyde per mole lysine group). The reaction was conducted at room temperature for 2 hrs. The pH was then adjusted to 5.2 with formic acid. No enzymatic activity was lost during the procedure. To 10 g of the detergent described in example 1, 80 mg of the above formulation was added. As reference, 80 mg of the enzyme stock solution added to 10 g of the same detergent.

After 3 weeks, needle-shaped enzyme deposit was observed in the reference detergent, whereas no deposit could be observed in the detergent containing modified enzyme according to the invention.

Example 8

Glutaraldehyde was added to a solution of protease (Savinase ®) to prepare an aqueous solution containing 45 mg/g (1.6 µmole/g) of Savinase ® and 0.32 mg/g (3.2 µmole/g) of aldehyde (i.e. a ratio of aldehyde molecules to primary amino groups of 0.33). The solution also contained 35% propylene glycol, 0.7% $Ca^{++}$ and 2% formate. pH was adjusted to 8.0 and the solution was left to react at room temperature for five hours.

When 0.2% of the treated Savinase ® was added to a clear detergent of essentially the same composition as the detergent in Example 1 a slight haziness was observed after 1 week at 35° C., whereas the untreated enzyme caused a slight precipitate (same formulation, dosage and storage conditions). When stored at 4° C. for 4 weeks the same pattern was observed: The treated enzyme gave a slight haziness in the detergent, but the untreated gave a marked precipitation.

We claim:

1. A liquid enzymatic detergent composition comprising
   (a) a modified enzyme dissolved therein, which is produced by modifying a detergent enzyme having at least one primary amino group by (i) reaction with an aldehyde, (ii) acylation with an acylating agent or (iii) alkylation with an alkylating agent; wherein a molecule of said modified enzyme contains one molecule of said detergent enzyme; and
   (b) a surfactant.

2. The liquid detergent composition according to claim 1, wherein said modified enzyme is present at a concentration at which said detergent enzyme is not soluble.

3. The liquid detergent composition according to claim 1, wherein said detergent enzyme is a Bacillus protease.

4. The liquid detergent composition according to claim 3, wherein said detergent enzyme is subtilisin Carlsberg.

5. The liquid detergent composition according to claim 1, wherein said aldehyde is formaldehyde.

6. The liquid detergent composition according to claim 1, wherein said aldehyde is glutaraldehyde or o-phthaldialdehyde.

7. The liquid detergent composition according to claim 1, wherein said acylation is done by treatment with acetic, propionic, butyric, valeric or caprylic anhydride.

8. The liquid detergent composition according to claim 1, wherein said acylation is done by treatment with maleic or succinic anhydride.

9. The liquid detergent composition according to claim 1, wherein said alkylation is achieved by reductive aldehyde treatment.

10. The liquid detergent composition according to claim 9, wherein said aldehyde is formaldehyde.

11. The liquid detergent composition according to claim 9, wherein said aldehyde is glutaraldehyde or o-phthaldialdehyde.

12. A liquid enzymatic detergent additive comprising
   (a) a modified enzyme dissolved therein, which is produced by modifying a detergent enzyme having at least one primary amino group by (i) reaction with an aldehyde, (ii) acylation with an acylating agent or (iii) alkylation with an alkylating agent; wherein said enzyme is a monomer; and
   (b) an enzyme stabilizer.

13. The detergent additive according to claim 12, wherein said detergent enzyme is a Bacillus protease.

14. The detergent additive according to claim 13, wherein said detergent enzyme is subtilisin Carlsberg.

15. The liquid detergent additive according to claim 12, wherein said aldehyde is formaldehyde.

16. The liquid detergent additive according to claim 12, wherein said aldehyde is glutaraldehyde or o-phthaldialdehyde.

17. The liquid detergent additive according to claim 12, wherein said acylation is done by treatment with acetic, propionic, butyric, valeric or caprylic anhydride.

18. The liquid detergent additive according to claim 12, wherein said acylation is done by treatment with maleic or succinic anhydride.

19. The liquid detergent additive according to claim 12, wherein said alkylation is achieved by reductive aldehyde treatment.

20. The liquid detergent additive according to claim 19, wherein said aldehyde is formaldehyde.

21. The liquid detergent additive according to claim 19, wherein said aldehyde is glutaraldehyde or o-phthaldialdehyde.

22. The detergent additive according to claim 12, wherein said enzyme stabilizer is a polyol.

23. A method of increasing the solubility of a detergent enzyme having one or more primary amino groups in a liquid detergent, comprising modifying at least one of said primary amino groups by (i) reaction with an aldehyde, (ii) acylation with an acylating agent or (iii) alkylation with an alkylating agent; to produce a modified enzyme, wherein a molecule of said modified enzyme contains one molecule of said detergent enzyme.

24. The method according to claim 23, wherein said detergent enzyme contains at least 4 primary amino groups.

25. The method according to claim 23, wherein said detergent enzyme is an alkaline Bacillus protease.

26. The method according to claim 25, wherein said detergent enzyme is subtilisin Carlsberg.

27. The method according to claim 23, wherein said modification is done by treatment with a bi- or polyfunctional reagent in a molar ratio of functional groups of said reagent to said primary amino groups between 0.1 and 1.0.

28. The method according to claim 27, wherein said bifunctional reagent is glutaraldehyde, o-phthalic aldehyde, maleic anhydride or succinic anhydride.

29. The method according to claim 23, wherein said detergent enzyme is modified by treatment with a monofunctional reagent at a molar ratio of said reagent to said primary amino groups between 1 and 5.

30. The method according to claim 29, wherein said monofunctional reagent is acetic, propionic, butyric, valeric or caprylic anhydride or formaldehyde.

31. The method according to claim 23, wherein said alkylation is achieved by reductive aldehyde treatment.

32. A method of preparing a liquid product comprising
   (a) modifying at least one primary amino group of a detergent enzyme by (i) reaction with an aldehyde, (ii) acylation with an acylating agent or (iii) alkylation with an alkylating agent; to produce a modified enzyme, wherein a molecule of said modified enzyme contains one molecule of said detergent enzyme; and
   (b) providing said modified enzyme into the liquid product.

33. The method according to claim 32, wherein said liquid product is a liquid detergent composition or a liquid detergent additive.

* * * * *